United States Patent
Colman et al.

(10) Patent No.: US 10,508,311 B2
(45) Date of Patent: Dec. 17, 2019

(54) SINGLE MOLECULE-OVERLAPPING READ ANALYSIS FOR MINOR VARIANT MUTATION DETECTION IN PATHOGEN SAMPLES

(71) Applicants: THE TRANSLATIONAL GENOMICS RESEARCH INSTITUTE, Phoenix, AZ (US); ARIZONA BOARD OF REGENTS ON BEHALF OF NORTHERN ARIZONA UNIVERSITY, Flagstaff, AZ (US); THE REGENTS OF THE UNIVERSITY OF CALIFORNIA, Oakland, CA (US)

(72) Inventors: Rebecca E. Colman, Flagstaff, AZ (US); David M. Engelthaler, Flagstaff, AZ (US); James M. Schupp, Flagstaff, AZ (US); Paul Keim, Flagstaff, AZ (US); David Smith, Flagstaff, AZ (US); Antonino Catanzaro, San Diego, CA (US); Timothy Rodwell, San Diego, CA (US)

(73) Assignees: The Translational Genomics Research Institute, Phoenix, AZ (US); Arizona Board of Regents on behalf of Northern Arizona University, Flagstaff, AZ (US); The Regents of The University of California, Oakland, CA (US)

( * ) Notice: Subject to any disclaimer, the term of this patent is extended or adjusted under 35 U.S.C. 154(b) by 689 days.

(21) Appl. No.: 14/912,918

(22) PCT Filed: Aug. 26, 2014

(86) PCT No.: PCT/US2014/052745
§ 371 (c)(1),
(2) Date: Feb. 18, 2016

(87) PCT Pub. No.: WO2015/031385
PCT Pub. Date: Mar. 5, 2015

(65) Prior Publication Data
US 2016/0201115 A1    Jul. 14, 2016

Related U.S. Application Data

(60) Provisional application No. 61/870,220, filed on Aug. 26, 2013.

(51) Int. Cl.
| G01N 33/48 | (2006.01) |
| C12Q 1/689 | (2018.01) |
| G16B 30/00 | (2019.01) |
| C12Q 1/6858 | (2018.01) |

(52) U.S. Cl.
CPC ........... *C12Q 1/689* (2013.01); *C12Q 1/6858* (2013.01); *G16B 30/00* (2019.02); *C12Q 2600/106* (2013.01); *C12Q 2600/156* (2013.01)

(58) Field of Classification Search
None
See application file for complete search history.

(56) References Cited

U.S. PATENT DOCUMENTS

| 2007/0264642 | A1  | 11/2007 | Willis et al. | |
| 2010/0323348 | A1* | 12/2010 | Hamady | C12Q 1/6874 435/6.11 |
| 2011/0207134 | A1* | 8/2011  | Faham  | C12Q 1/6886 435/6.11 |
| 2012/0088684 | A1* | 4/2012  | Liu    | C12Q 1/6844 506/9 |
| 2012/0264726 | A1* | 10/2012 | Benjamin | A61K 9/0014 514/197 |
| 2014/0227706 | A1  | 8/2014  | Kato et al. | |

(Continued)

FOREIGN PATENT DOCUMENTS

| WO | 2010/020618 A1 | 2/2010 |
| WO | 2011156795 A2 | 12/2011 |

OTHER PUBLICATIONS

Adjers, et al., "Susceptibility testing with the manual mycobacteria growth indicator tube (MGIT) and the MGIT 960 system provides rapid and reliable verification of multidrug-resistant tuberculosis," J Clinical Microbiology, 41(3):1235-9 (Mar. 2003).

(Continued)

*Primary Examiner* — Anna Skibinsky
(74) *Attorney, Agent, or Firm* — Rodney J. Fuller; Booth Udall Fuller, PLC (57) ABSTRACT

The present invention provides a method of detecting a heteroresistant population of a pathogen in a sample, the method comprising: a) providing a sample comprising a population of a pathogen; b) extracting nucleic acids from the sample; c) amplifying a target locus of the genome of the pathogen in the extracted nucleic acids, wherein the target locus comprises at least one minor variant associated with drug resistance in the pathogen; d) consecutively sequencing both overlapping nucleic acid strands from a single DNA molecule amplified from the target locus on a Next Generation Sequencing (NGS) platform; e) applying an alignment algorithm to sequencing data from the overlapping nucleic acid strands; and f) performing an analysis of the aligned sequencing data to detect the at least one minor variant and heteroresistant population of the pathogen.

16 Claims, 4 Drawing Sheets
Specification includes a Sequence Listing.

(56) References Cited

U.S. PATENT DOCUMENTS

2015/0376683 A1* 12/2015 Weir .................... C12Q 1/6883
506/9

OTHER PUBLICATIONS

Ajbani, et al., "Evaluation of genotype MTBDRsl assay to detect drug resistance associated with fluoroquinolones, aminoglycosides and ethambutol on clinical sediment," PLoS One 2012;7(11):e49433 (Nov. 15, 2012).

Beauchemin, et al., "Modeling amantadine treatment of influenza A virus in vitro," J Theor Biol. 2008;254(2):439-51. PMCID: 2663526.

CDC, FluView: A Weekly Influenza Surveillance Report Prepared by the Influenza Division; 2009-2010 Influenza Season: Week 50 ending Dec. 19, 2009, Centers for Disease Control and Prevention, http://wwwcdcgov/flu/weekly/, accessed at https://www.cdc.gov/flu/weekly/pdf/External_F0950.pdf (2009).

CDC, "Oseltamivir-resistant novel influenza A (H1N1) virus infection in two immunosuppressed patients—Seattle, Washington, 2009," MMWR Morb Mortal Wkly Rep., Centers for Disease Control and Prevention, 58(32):893-6 (Aug. 14, 2009).

Chen-Harris, et al., "Ultra-deep mutant spectrum profiling: improving sequencing accuracy using overlapping read pairs," BMC Genomics, 14:96. PMCID: 3599684 (2013).

Colijn, et al., "Spontaneous emergence of multiple drug resistance in tuberculosis before and during therapy," PLoS One. 2011;6(3):e18327 (Mar. 30, 2011).

Colman, et al., "Haplotype analysis for Bacterial Rare Variant Detection," 11th Annual ASM Biodefense and Emerging Diseases Research Meeting, Washington, DC, (Feb. 25-27, 2013).

Colman, et al., "Advancing heteroresistance detection in tuberculosis using single-molecule-overlapping read (SMOR) analysis," Infectious Diseases Society of America, IDSA Conference, San Francisco, CA, (Oct. 5, 2013).

Cullen, et al., "Direct detection of heteroresistance in *Mycobacterium tuberculosis* using molecular techniques," Journal of Medical Microbiology, 55(Pt 8):1157-8 (2006).

Cushing et al., "RVD: a command-line program for ultrasensitive rare single nucleotide variant detection using targeted next-generation DNA resequencing," BMC Research Notes, 6(1):206 (2013).

Duwe et al. "A new and rapid genotypic assay for the detection of neuraminidase inhibitor resistant influenza A viruses of subtype H1N1, H3N2, and H5N1," Journal of Virological Methods, 153(2):134-41 (2008).

Ellebedy, et al., "Influenza vaccines," Vaccine, 2009;27 Suppl 4:D65-8 (Nov. 5, 2009).

Flaherty, et al., "Ultrasensitive detection of rare mutations using next-generation targeted resequencing," Nucleic Acids Research, 2012;40(1):e2 (Oct. 19, 2011).

Folkvardsen, et al., "Can molecular methods detect 1% isoniazid resistance in *Mycobacterium tuberculosis*?" Journal of Clinical Microbiology, 2013;51(5):1596-9 (May 2013).

Fordyce, et al., "Genetic diversity among pandemic 2009 influenza viruses isolated from a transmission chain," Virology Journal, 10:116. PMCID: 3639878 (2013).

Gandhi, et al., "Multidrug-resistant and extensively drug-resistant tuberculosis: a threat to global control of tuberculosis" Lancet. 2010;375(9728):1830-43.

Gillespie, Stephen H., "Evolution of drug resistance in *Mycobacterium tuberculosis*: clinical and molecular perspective," Antimicrobial Agents and Chemotherapy, 2002;46(2):267-74 (Feb. 2002).

Hayden, Frederick, "Developing new antiviral agents for influenza treatment: what does the future hold?" Clinical Infectious Diseases, 2009;48 Suppl 1:S3-S13.

Hoopes, et al., "Triple combination antiviral drug (TCAD) composed of amantadine, oseltamivir, and ribavirin impedes the selection of drug-resistant influenza A virus." PLoS One. 2011;6(12):e29778. PMCID: 3248427 (Dec. 29, 2011).

Huse, et al., "Accuracy and quality of massively parallel DNA pyrosequencing," Genome Biology, 2007;8(7):R143 (Jul. 20, 2007).

Jonsson, et al., "Will molecular diagnosis of drug-resistant tuberculosis improve patient outcomes?" Int J Tuberc Lung Dis., 2012;16(1):4-5.

Kampmann, et al., "A simple method for the parallel deep sequencing of full influenza A genomes," Journal of Virological Methods, 2011;178(1-2):243-8 (Sep. 17, 2011).

Karahan, et al., "Restriction endonuclease analysis as a solution for determining rifampin resistance mutations by automated DNA sequencing in heteroresistant *Mycobacterium tuberculosis* strains," Microbial Drug Resistance, 2005;11(2):137-40.

Kunisaki, et al., "Influenza in immunosuppressed populations: a review of infection frequency, morbidity, mortality, and vaccine responses," Lancet Infect Dis. 2009;9(8):493-504.

Larder, et al., "Quantitative detection of HIV-1 drug resistance mutations by automated DNA sequencing," Nature, 1993;365(6447):671-3 (Oct. 14, 1993).

Lee, et al., "Viral loads and duration of viral shedding in adult patients hospitalized with influenza," The Journal of Infectious Diseases, 2009;200(4):492-500.

Lipstich, et al., "Population dynamics of tuberculosis treatment: mathematical models of the roles of non-compliance and bacterial heterogeneity in the evolution of drug resistance," The International Journal of Tuberculosis and Lung Disease, 1998;2(3):187-99.

Liu, et al., "Rapid quantification of single-nucleotide mutations in mixed influenza A viral populations using allele-specific mixture analysis," Journal of Virological Methods, 2010;163(1):109-15.

Long et al., "PoolHap: inferring haplotype frequencies from pooled samples by next generation sequencing," PLoS One. 2011;6(1):e15292 (Jan. 5, 2011).

McCullers, et al., "Multiple Genotypes of Influenza B Virus Circulated between 1979 and 2003," Journal of Virology, 2004;78(23)12817-28 (Dec. 2004).

Migliori, et al., "First tuberculosis cases in Italy resistant to all tested drugs," Eurosurveillance. 2007;12(5).

Molinari, et al., "The annual impact of seasonal influenza in the US: measuring disease burden and costs," Vaccine, 2007;25(27):5086-96 (Apr. 20, 2007).

Mordandi et al., "Allele specific locked nucleic acid quantitative PCR (ASLNAqPCR): an accurate and cost-effective assay to diagnose and quantify KRAS and BRAF mutation." PLoS One. 2012;7(4):e36084 (Apr. 30, 2012).

Nakamura, et al., "Sequence-specific error profile of Illumina sequencers." Nucleic Acids Research, 2011;39(13): e90-e (May 16, 2011).

Nguyen, et al. Triple combination of amantadine, ribavirin, and oseltamivir is highly active and synergistic against drug resistant influenza virus strains in vitro. PLoS One. 2010;5(2):e9332.

Nguyen, et al., "Triple combination of oseltamivir, amantadine, and ribavirin displays synergistic activity against multiple influenza virus strains in vitro," Antimicrobial Agents and Chemotherapy. 2009;53(10):4115-26 (Oct. 2009).

Nguyen, et al., "Efficacy of combined therapy with amantadine, oseltamivir, and ribavirin in vivo against susceptible and amantadine-resistant influenza A viruses," PLoS One. 2012;7(1):e31006. PMCID: 3264642 (Jan. 23, 2012).

WHO, "Policy guidance on drug-susceptibility testing (DST) of second-line antituberculosis drugs," World Health Organization, Geneva, Switzerland, (2008).

Rinder, et al., "Heteroresistance in *Mycobacterium tuberculosis*," The International Journal of Tuberculosis and Lung Disease, 2001;5(4):339-45.

Rinder, Heinz, Hetero-resistance: an under-recognised confounder in diagnosis and therapy?, J Med Microbiol. 2001;50(12):1018-20.

Rutvisuttinunt, et al., "Simultaneous and complete genome sequencing of Influenza A and B with high coverage by Illumina MiSeq Platform," Journal of Virological Methods, 193: 394-404 (Jul. 12, 2013).

Saunders, et al., "Deep resequencing of serial sputum isolates of *Mycobacterium tuberculosis* during therapeutic failure due to poor compliance reveals stepwise mutation of key resistance genes on an otherwise stable genetic background." Journal of Infection. 2011;62(3):212-7 (Jan. 13, 2011).

(56) References Cited

OTHER PUBLICATIONS

Schmitt, et al., "Detection of ultra-rare mutations by next-generation sequencing," Proceedings of the National Academy of Sciences of the United States of America, 2012;109(36):14508-13 (Sep. 4, 2012).
Seo, et al., "Combination therapy with amantadine, oseltamivir and ribavirin for influenza A infection: safety and pharmacokinetics," Antivir Ther. 2013;18(3):377-86.
Shah, et al., "Increasing drug resistance in extensively drug-resistant tuberculosis, South Africa.," Emerging Infect Dis., 2011;17(3):510-3 (Mar. 2011).
Shendure, et al., "Next-generation DNA sequencing," Nature Biotechnology, 2008;26(10):1135-45 (Oct. 2008).
Streicher, et al., "*Mycobacterium tuberculosis* population structure determines the outcome of genetics-based second-line drug resistance testing," Antimicrobial Agents and Chemotherapy, 2012;56(5):2420-7.
Sundstrom, et al., "KRAS analysis in colorectal carcinoma: analytical aspects of Pyrosequencing and allele-specific PCR in clinical practice," BMC Cancer, 2010;10:660 (Dec. 1, 2010).
Tolani, et al., "Drug resistance mutations and heteroresistance detected using the GenoType MTBDRplus assay and their implication for treatment outcomes in patients from Mumbai, India," BMC Infectious Diseases, 2012;12:9.
Deng, Jie et al., "Targeted bisulfite sequencing reveals changes in DNA methylation associated with nuclear reprogramming", Nature Biotechnology, 27(4):353-360 (Apr. 1, 2009).
Li, J. B. et al., "Multiplex padlock targeted sequencing reveals human hypermutable CpG variations", Genome Research, 19(9):1606-1615 (Sep. 1, 2009).
Chakravorty, Soumitesh et al., "Rapid, High-Throughput Detection of Rifampin Resistance and Heteroresistance in *Mycobacterium tuberculosis* by Use of Sloppy Molecular Beacon Melting Temperature Coding", Journal of Clinical Microbiology, 50(7)2194-2202 (Jul. 2012).
Pholwat, Supom et al., "Digital PCR to Detect and Quantify Heteroresistance in Drug Resistant *Mycobacterium tuberculosis*", Plos One, 8(2):e57238, pp. 1-11 (Feb. 2013).
Udwadia, et al., "Totally drug-resistant tuberculosis in India," Clin Infect Dis. 2012;54(4):579-81.

Velayati, et al., "Emergence of new forms of totally drug-resistant tuberculosis bacilli: super extensively drug-resistant tuberculosis or totally drug-resistant strains in Iran," Chest. 2009;136(2):420-5.
Watson, et al., "Viral population analysis and minority-variant detection using short read next-generation sequencing," Philos Trans R Soc Lond B Biol Sci, 2013;368(1614):20120205. PMCID: 3678329.
Woods, et al., "Susceptibility testing of mycobacteria, nocardiae, and other aerobic actinomycetes; approved standard," NCCLS (2003).
Zhang, et al., "Subpopulation analysis of heteroresistance to fluoroquinolone in *Mycobacterium tuberculosis* solates from Beijing, China," J Clin Microbiol. 2012;50(4):1471-4.
WHO, "Global tuberculosis control: WHO Report 2011," World Health Organization (2011).
WHO, "Multidrug and extensively drug-resistant TB (M/XDR-TB): 2010 global report on surveillance and response," World Health Organization (2010).
Chen-Harris, Haiyin et al., "Ultra-deep mutant spectrum profiling: improving sequencing accuracy using overlapping read pairs", BMC Genomics, 14(96):1-13 (2013).
Daum et al., "Next-Generation Ion Torrent Sequencing of Drug Resistance Mutations in *Mycobacterium tuberculosis* Strains", Journal of Clinical Microbiology, 50(12):3831-3837 (Dec. 1, 2012).
Engstrom et al., "Detection of Heteroresistant *Mycobacterium tuberculosis* by Pyrosequencing", Journal of Clinical Microbiology, 51(12):4210-4212 (Sep. 18, 2013).
Moller et al., "Analysis of eight genes modulating interferon gamma and human genetic susceptibility to tuberculosis: a case-control association study", BMC Infectious Diseases, 10:1-9 (Jun. 7, 2010).
Sengstake et al., "Optimizing multiplex SNP-based data analysis for genotyping of *Mycobacterium tuberculosis* isolates", BMC Genomics, 15:1-11 (Jul. 7, 2014).
Zhang et al., "Co-occurrence of amikacini-resistant and-susceptible *Mycobacterium tuberculosis* isolates in clinical samples from Beijing, China", Journal of Antimicrobial Chemotherapy, 68:1-6 (Mar. 28, 2013).
International Search Report for PCT/US2014/052745 dated Dec. 24, 2014.
Written Opinion of the International Searching Authority for PCT/US2014/052745 dated Dec. 24, 2014.
International Preliminary Report on Patentability for PCT/US2014/052745 dated Mar. 1, 2016.

* cited by examiner

FIG. 3 gyrA 7585G-C variant

FIG. 4

SINGLE MOLECULE-OVERLAPPING READ ANALYSIS FOR MINOR VARIANT MUTATION DETECTION IN PATHOGEN SAMPLES

CROSS-REFERENCE TO RELATED APPLICATIONS

The present application is the U.S. National Stage International Application No. PCT/US2014/052745, filed Aug. 26, 2014, which claims the benefit of U.S. Provisional Application No. 61/870,220 filed on Aug. 26, 2013, the contents of each of which are hereby incorporated by reference in their entireties.

STATEMENT REGARDING FEDERALLY SPONSORED RESEARCH OR DEVELOPMENT

This invention was made with government support under AI082229 awarded by the National Institutes for Health. The government has certain rights in this invention.

INCORPORATION-BY-REFERENCE OF MATERIAL ELECTRONICALLY FILED

Incorporated by reference in its entirety herein is a computer-readable nucleotide sequence listing submitted concurrently herewith and identified as follows: One 1,761 byte ASCII (text) file named "91482_137_Sequence_Listing.txt" created on Aug. 26, 2014.

TECHNICAL FIELD

The present invention relates to diagnostic methods for the detection and treatment of heteroresistant populations of pathogens.

BACKGROUND

Heteroresistance, the simultaneous occurrence of drug resistant subpopulations in an otherwise drug susceptible bacterial population in a patient sample, has created uncertainty in the treatment and diagnosis of tuberculosis (TB) and is thought to be an important driver of multi-drug resistance in *Mycobacterium tuberculosis* (Mtb) which is a significant threat to global TB control given its broadening distribution and the emergence of what is being called "totally drug-resistant TB" (TDR-TB). It has been well-documented that heteroresistance creates difficulties in the interpretation of rapid molecular drug resistance tests because it leads to 'indeterminate' test results, but the clinical significance of heteroresistance is still being evaluated. Previously undetectable levels of Mtb resistant subpopulations within a larger population of susceptible pathogens (i.e., heteroresistance) may be present in as many as 20% of TB patients, and might help explain some of the inconsistency observed in TB treatment outcomes. Previously, there was no accurate means of quantifying heteroresistance dynamics or even detecting the presence of heteroresistance until the resistant sub-population had expanded to >1% of the pathogen population within a clinical sample. At that point, however, the patient's infection was determined to be resistant for the purposes of treatment and a potential window of opportunity for preventing resistance was closed.

The current gold standard method for Mtb drug susceptibility testing (DST) can be used to detect later stages of heteroresistance. This phenotypic test uses a culture-based, indirect proportion method which relies on the detection of growth of >1% of the inoculum on culture medium containing a critical concentration of an anti-TB drug. It is estimated that for every $10^{7-8}$ Mtb bacilli there is at least one bacillus that has a genetic mutation that renders it naturally resistant to a particular drug. Suboptimal antibiotic treatment causes the few Mtb naturally resistant mutants (by definition, a certain level of heteroresistance) to gain a competitive advantage and subsequently dominate the lesion. The 1% population component of resistant organisms that is detectable by the DST method is well above naturally occurring Mtb resistance mutation rates and, again, detections at this level are typically too late to prevent treatment failure.

Current diagnostic methods are limited in their use and efficacy. The threshold of in vitro Mycobacteria Growth Indicator Tube (MGIT) heteroresistance detection is approximately 1% of the population, but is qualitative and takes weeks to complete. Current molecular tools that detect resistance-conferring mutations in Mtb coding genes and promoter regions which also have the potential to rapidly detect heteroresistance, include DNA sequencing (Sanger and pyrosequencing) and allele specific PCR analysis, but these methods are not sensitive or have limited gene coverage. Sanger sequencing and pyrosequencing each have significant technical limitations for analyzing mixed populations. Sanger sequencing has a well-established detection threshold of ~25% minor component in a mixed sample and relies on subjective visual evaluation of the electropherogram for "quantification". Pyrosequencing (e.g., Qiagen Pyromark) is capable of true quantitative sequencing, but has a reported quantification threshold of detection equal to 2.5%-5% of an Mtb population and has limited sequencing depth capability. The PCR-hybridization approach of the line-probe assay has a described sensitivity of detection of a minor resistant variant detection at 5%. Detection of heteroresistance, even at the 1% level provided by MGIT-DST, is insufficient and likely too late to prevent treatment failure. A quantitative and more sensitive method is highly desirable.

Mtb heteroresistance is not a rare phenomenon, occurring in 9-30% of Mtb populations studied, and has been identified in Mtb populations with phenotypic resistance to first line-drugs (INH, RIF, ETH, and STR) and second-line fluoroquinolones (ofloxacin-OFX) and injectables (AMK). It is highly likely that drug resistant organisms are present in most TB lesions, even as very minor population components, given the high bacilli loads that are typically found in patients.

There is also a critical need to detect minor resistance variant populations in clinical samples early in therapy to allow for customizable patient treatment and to track variant populations' progress through time. The present invention addresses this need by providing methods to detect heteroresistance in TB patient samples at low resistance levels using multiple target loci amplification and sequencing with clinically relevant next generation technology. This translates to a significant increase in the level of detection sensitivity as compared to other methods and an enhanced ability to treat patients with effective therapies against the resistant pathogen populations.

SUMMARY

In some embodiments, the present invention is directed to a method of detecting a heteroresistant population of a pathogen in a sample, the method comprising: a) providing a sample comprising a population of a pathogen; b) extracting nucleic acids from the sample; c) amplifying a target locus of the genome of the pathogen in the extracted nucleic acids, wherein the target locus comprises at least one minor variant associated with drug resistance in the pathogen; d) consecutively sequencing both overlapping nucleic acid strands from a single DNA molecule amplified from the target locus on a Next Generation Sequencing (NGS) platform; e) applying an alignment algorithm to sequencing data from the overlapping nucleic acid strands; and f) performing an analysis of the aligned sequencing data to detect the at least one minor variant and heteroresistant population of the pathogen. In certain embodiments, both overlapping nucleic acid strands refers to the coding strand and the noncoding strand of a gene (e.g., a resistance gene such as, but not limited torrs, katG, inhA, and gyrA).

In some implementations, the analysis of the aligned sequencing data is a minor variant analysis. In certain aspects, the minor variant analysis is a haplotype variant analysis. The target locus may be amplified with a high fidelity polymerase such as KAPA HiFi™ DNA polymerase or Q5® HIFI DNA polymerase.

In some aspects, each of the overlapping nucleic acid strands consists of less than about 500 nucleotides, less than about 450 nucleotides, less than about 400 nucleotides, less than about 350 nucleotides, less than about 300 nucleotides, less than about 250 nucleotides, less than about 200 nucleotides, less than about 150 nucleotides, less than about 100 nucleotides, or less than about 50 nucleotides.

In other aspects, the alignment algorithm is optimized for short nucleotide space reads of less than about 500 nucleotides, less than about 450 nucleotides, less than about 400 nucleotides, less than about 350 nucleotides, less than about 300 nucleotides, less than about 250 nucleotides, less than about 200 nucleotides, less than about 150 nucleotides, less than about 100 nucleotides, or less than about 50 nucleotides. The alignment algorithm may be Novoalign. Various NGS platforms may be used with the present invention including the Ilumina MiSeq platform.

In some aspects, the minor variant analysis is performed with a bioinformatics script that requires a user to input genomic regions of interest and generates a report with single molecule-overlapping read information used to identify the minor variant.

In yet other aspects, the methods of the present invention further comprise using a highly homogenous synthetic plasmid standard to identify actual sequence error rate variance between target loci and sequencing runs.

In some embodiments, the minor variant is selected from the group consisting of a single nucleotide polymorphism (SNP), an insertion, and a deletion.

In other embodiments, the pathogen is *Mycobacterium tuberculosis*. In these embodiments, the at least one minor variant may be located within a genomic sequence selected from the group consisting of katG, inhA promoter, rpoB, gyrA, rrs, eis promoter, and combinations thereof.

In certain aspects, the heteroresistant population is resistant to isoniazid (INH), rifampin (RIF), moxifloxacin (MOX), amikacin (AMK), kanamycin (KAN) and/or capreomycin (CAP).

In some embodiments, the present invention is directed to methods of treating a subject in need thereof with a therapeutic agent to a heteroresistant population of *M. tuberculosis*, wherein the therapeutic agent is selected from the group consisting of PA-824, OPC-67683, SQ109, TMC207, NAS-21, NAS-91, thioridazine, chlorpromazine, and a 1,3-benzothiazin-4-one, and combinations thereof. In certain aspects, the treatment is preceded by the detection of one or more heteroresistant population of *M. tuberculosis* in a sample from the subject.

BRIEF DESCRIPTION OF THE DRAWINGS

Illustrative and exemplary embodiments of the invention are shown in the drawings in which.

Elements and facts in the figures are illustrated for simplicity and have not necessarily been rendered according to any particular sequence or embodiment.

DETAILED DESCRIPTION

Aspects and applications of the invention presented herein are described below in the drawings and detailed description of the invention. Unless specifically noted, it is intended that the words and phrases in the specification and the claims be given their plain, ordinary, and accustomed meaning to those of ordinary skill in the applicable arts.

In the following description, and for the purposes of explanation, numerous specific details are set forth in order to provide a thorough understanding of the various aspects of the invention. It will be understood, however, by those skilled in the relevant arts, that the present invention may be practiced without these specific details. The full scope of the inventions is not limited to the specific examples that are described below.

As used herein, the verb "comprise" as is used in this description and in the claims and its conjugations are used in its non-limiting sense to mean that items following the word are included, but items not specifically mentioned are not excluded. In addition, reference to an element by the indefinite article "a" or "an" does not exclude the possibility that more than one of the elements are present, unless the context clearly requires that there is one and only one of the elements. The indefinite article "a" or "an" thus usually means "at least one".

As used herein, a "sample," such as a biological sample that includes nucleic acid molecules, is a sample obtained from a subject. As used herein, biological samples include all clinical samples including, but not limited to, cells, tissues, and bodily fluids, such as: blood; derivatives and fractions of blood, such as serum; extracted galls; biopsied or surgically removed tissue, including tissues that are, for example, unfixed, frozen, fixed in formalin and/or embedded in paraffin; tears; milk; skin scrapes; surface washings; urine; sputum; cerebrospinal fluid; prostate fluid; pus; or bone marrow aspirates. In a particular example, a sample includes blood obtained from a human subject, such as whole blood or serum. In another particular example, a sample includes buccal cells, for example collected using a swab or by an oral rinse.

In some embodiments, the present invention is directed to a next-generation sequencing analysis methodology to detect minor proportions of a sample that contain mutations associated with important phenotypes, including antibacterial and antiviral resistance. This analysis decreases the sequencing error rate so that extremely low levels of true minor components (e.g., SNP loci) can be detected.

The incidence of drug-resistant (DR) tuberculosis (TB) continues to increase worldwide. Undetected heteroresistance, the presence of DR and susceptible genotypes in bacterial populations involved in infection, at treatment initiation may play a role in the expansion of DR strains and treatment failure. In *Mycobacterium tuberculosis*, current minor DR component detection levels are limited to ~1%, using phenotypic drug susceptibility testing, which requires 15-30 days or even longer to complete. By that point during an infection, it is likely too late to prevent DR-TB and treatment failure.

In some aspects, the present invention relates to a method of detecting resistant Mtb sub-populations consisting of 0.1% or less of the total Mtb population in under a week. Detection of minor components in complex biological mixtures has radically advanced with the emergence of next-generation sequencing. Low-level detection from sequence data, however, is not trivial, primarily due to the error rates in sequencing. The error associated with the respective sequencing platform, as well as the GC content of the organism, sets the limit of discerning actual minor component from error. However, the use of "single molecule-overlapping reads" (SMOR) analysis for determination of actual mutation ratios in target loci (e.g., antibiotic resistance genes) leads to an increase in heteroresistance detection sensitivity and lower error bias.

The use of overlapping reads allows for effective coverage of each locus on both strands of an individual sequenced DNA molecule, which in turn allows for an independent confirmation of the specific nucleotide at that single locus. The product rule of probability applies, such that if one locus on a single molecule is read two times, it has the lower limit of detection of the probability of one error occurring squared. In some embodiments, the Illumina Miseq platform is used to sequence amplicons from several different in vitro mixtures of DR and susceptible Mtb strains to validate the use of SMOR for identifying heteroresistance. The calculated average of combined amplification and sequencing error rate for Mtb (a high GC organism) is 0.51% per position across the amplicons tested. When employing SMOR, the theoretical limit of detection of a minor component is $2.6 \times 10^{-6}$, readily allowing for detection of minor components below 0.51%.

The Inventors have been able to detect a 0.3% artificial mixture of SNP alleles in the inhA promoter at a frequency of $3.07 \times 10^{-3}$, which was at least two orders of magnitude more frequent than identifiable sequence errors. The use of SMOR allows for researchers and clinicians to follow the evolution of heteroresistance, determine its clinical relevance and develop appropriate treatment strategies to suppress minor component resistant sub-populations before they become clinically significant.

In *Mycobacteria tuberculosis* (Mtb) there are characterized SNPs that confer resistance to several different antibiotics. By using overlapping reads on these targeted regions we can characterize heteroresistance in clinical samples down to a level that has not been previously achieved. Overlapping reads have been used in next generation sequencing to improve whole genome examination but they have not been used to add confidence in antibiotic resistance population evaluation.

With the invention, clinicians are able to track patient treatment in a more timely fashion and alter the course of treatment when heteroresistance is detected within a week versus a month or more as is common with current technology. This analysis can also be useful to researchers wanting to characterize population structure within a single sample of bacteria.

In one embodiment, the invention provides a diagnostic assay for the detection of heteroresistance in *Mycobacterium tuberculosis* in clinical samples. Modifications of this assay can be used for low level minor mutation resistance in other organisms, as we have also demonstrated with influenza.

In some embodiments, the limit of detection for the minor variant is less than about 1.0%, less than about 0.9%, less than about 0.8%, less than about 0.7%, less than about 0.6%, less than about 0.5%, less than about 0.4%, less than about 0.3%, less than about 0.2%, less than about 0.1%, less than about 0.09%, less than about 0.08%, less than about 0.07%, less than about 0.06%, less than about 0.05%, less than about 0.04%, less than about 0.03%, less than about 0.02%, or less than about 0.01% of the heteroresistant population.

In other embodiments, each of the overlapping nucleic acid strands to be sequenced with the disclosed method consists of less than about 500 nucleotides, less than about 450 nucleotides, less than about 400 nucleotides, less than about 350 nucleotides, less than about 300 nucleotides, less than about 250 nucleotides, less than about 200 nucleotides, less than about 150 nucleotides, less than about 100 nucleotides, or less than about 50 nucleotides.

In yet other embodiments, the disclosed method further comprises administering a therapeutic agent to a heteroresistant population of *M. tuberculosis*. Exemplary therapeutic agents are found in Da Silva et al. (2011) J. Antimicrob. Chemother. 66:1417.

The minor variant detected in the heteroresistant population of *M. tuberculosis* may be an SNP, an insertion, or a deletion. Non-limiting examples of genetic mutations associated with drug resistance in *M. tuberculosis* are found in Georghiou et al. (2012) PLoS ONE 7(3):e33275.

Figure 1:
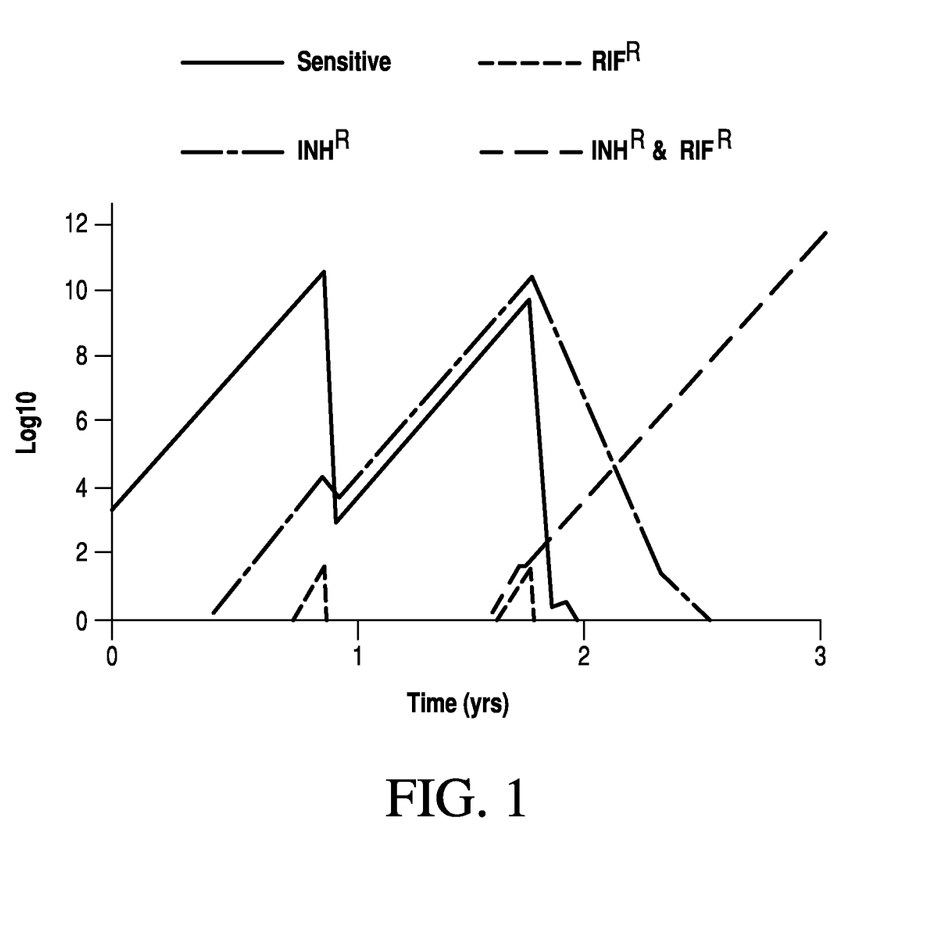
FIG. 1 depicts a model of heteroresistant dynamics of Mtb in a non-compliant patient.

Mathematical models of within-host Mtb population dynamics have predicted that heteroresistance can cause the emergence of MDR-TB prior to treatment initiation, and this emergence may occur 1,000-10,000 times more frequently. Studies of within-host dynamics of Mtb growth during treatment of have also indicated that resistant subpopulations can easily dominate a lesion over time in both treatment compliant and non-compliant patients (FIG. 1). The presence of resistance conferring mutations, even as minor components of an infecting population of Mtb, likely leads to selection of resistant strains, in the presence of the corresponding drug, and subsequent treatment failure. Minor resistant populations, however, are typically missed through standard analysis of isolates because the dominant organism phenotype masks any minor component variants. In certain aspects, the present invention addresses this problem by providing effective methods to detect and quantify minor resistant populations.

In some embodiments, the present invention is directed to the detection and analysis of heteroresistance in tuberculosis infections. An assay is provided that is able to accurately detect heteroresistance in Mtb and quantify the presence and proportion of all resistant allele minor components down to less than 0.1% using clinically relevant table-top next generation sequencing (NGS) technology and advanced bioinformatic algorithms. This approach provides a rapid, highly sensitive and specific method for detecting and monitoring the potential clinical relevance of heteroresistance in serial clinical samples from TB patients, which is not achievable by any other existing technology. Additionally, the NGS technology used in the assay can be used for deep sequencing of multiple targeted areas simultaneously, which allows for the detection of extremely rare minor components in a population at all targeted locations at once. This multiplexing approach is ideal for developing a practical, efficient and rapid analysis of heteroresistance directly from patient sputum, which has significant advantages over existing technologies.

While deep-sequencing seems to be an obvious solution, it is not sufficient, in and of itself. NGS minor variant detection is not trivial; primarily due to the error rates associated with the sequencing platform (e.g. Illumina MiSeq platform has a standard rating of 75% of bases having a 0.1% error). This rate sets a theoretical limit of discerning a rare variant from error but recent advances in technology and bioinformatics allow for minor variant detection at significantly lower levels than expected error rate. An advantage resulting from the approach of the present invention is the ability to accurately detect minor components below the sequencing error by using a "Single-Molecule Overlapping Read" (SMOR) analysis.

In certain aspects, the present invention relates to an approach to applying cutting-edge genomic science and technology to the ongoing clinical and public health problem of multi-drug resistant tuberculosis. In one embodiment, an optimized heteroresistance assay is used to detect known mutations associated with six anti-TB drugs, followed by an evaluation of heteroresistance in serial samples from a patient population.

In certain aspects, the population of bacteria comprises one or more bacteria selected from the group consisting of *Actinomedurae, Actinomyces israelii, Bacillus anthracis, Bacillus cereus, Clostridium botulinum, Clostridium difficile, Clostridium perfringens, Clostridium tetani, Corynebacterium, Enterococcus faecalis, Listeria monocytogenes, Nocardia, Propionibacterium acnes, Staphylococcus aureus, Staphylococcus epiderm, Streptococcus mutans, Streptococcus pneumonia, Afipia felis, Bacteroides, Bartonella bacilliformis, Bortadella pertussis, Borrelia burgdorferi, Borrelia recurrentis, Brucella, Calymmatobacterium granulomatis, Campylobacter, Escherichia coli, Francisella tularensis, Gardnerella vaginalis, Haemophilius aegyptius, Haemophilius ducreyi, Haemophilius influenziae, Heliobacter pylori, Legionella pneumophila, Leptospira interrogans, Neisseria meningitidia, Porphyromonas gingivalis, Providencia sturti, Pseudomonas aeruginosa, Salmonella enteridis, Salmonella typhi, Serratia marcescens, Shigella boydii, Streptobacillus moniliformis, Streptococcus pyogenes, Treponema pallidum, Vibrio cholerae, Yersinia enterocolitica, Yersinia pestis, Bartonella henselae, Chlamydia psittaci, Chlamydia trachomatis, Coxiella burnetii, Mycoplasma pneumoniae, Rickettsia akari, Rickettsia prowazekii, Rickettsia rickettsii, Rickettsia tsutsugamushi, Rickettsia typhi, Ureaplasma urealyticum, Diplococcus pneumoniae, Ehrlichia chafensis, Enterococcus faecium, Meningococci, Burkholderia mallei, Burkholderia pseudomallei, Ricinus communis,* and *Cryptosporidium parvum.*

In some embodiments, the present invention further comprises administering to the subject a regime of antibiotics to effectively control the population of pathogen based on the presence or absence of antibiotic resistance markers in the pathogen.

In certain aspects, the present invention is used to detect and monitor antibiotic resistance in a subject infected with a population of bacteria. Antibiotic resistance can be determined by the presence or absence of one or more antibiotic resistance genes or markers in the population. Non-limiting examples of such antibiotic resistance genes include $bla_{tem}$, $bla_{shv}$, $bla_{rob}$, $bla_{oxa}$, blaZ, aadB, aacC1, aacC2, aacC3, aac6'-IIa, aacA4, aad(6'), vanA, vanB, vanC, msrA, sarA, aac(6') aph(2"), vat, vga, ermA, ermB, ermC, mecA, int, sul, mecA, aac2ia, aac2ib, aac2ic, aac2id, aac2i, aac3ia, aac3iia, aac3iib, aac3iii, aac3iv, aac3ix, aac3vi, aac3viii, aac3vii, aac3x, aac6i, aac6ia, aac6ib, aac6ic, aac6ie, aac6if, aac6ig, aac6iia, aac6iib, aad9, aad9ib, aadd, acra, acrb, adea, adeb, adec, amra, amrb, ant2ia, ant2ib, ant3ia, ant4iia, ant6ia, aph33ia, aph33ib, aph3ia, aph3ib, aph3ic, aph3iiia, aph3iva, aph3va, aph3vb, aph3via, aph3viia, aph4ib, aph6ia, aph6ib, aph6ic, aph6id, ama, baca, bcra, bcrc, bl1_acc, bl1_ampc, bl1_asba, bl1_ceps, bl1_cmy2, bl1_ec, bl1_fox, bl1_mox, bl1_och, bl1_pao, bl1_pse, bl1_sm, bl2a_1, bl2a_exo, bl2a_iii2, bl2a_iii, bl2a_kcc, bl2a_nps, bl2a_okp, bl2a_pc, bl2be_ctxm, bl2be_oxyl, bl2be_per, bl2be_shv2, bl2b_rob, bl2b_tem1, bl2b_tem2, bl2b_tem, bl2b_tle, bl2b_ula, bl2c_bro, bl2c_pse1, bl2c_pse3, bl2d_lcr1, bl2d_moxa, bl2d_oxa10, bl2d_oxa1, bl2d_oxa2, bl2d_oxa5, bl2d_oxa9, bl2d_r39, bl2e_cbla, bl2e_cepa, bl2e_cfxa, bl2e_fpm, bl2e_y56, bl2f_nmca, bl2f_sme1, bl2_ges, bl2_kpc, bl2_len, bl2_veb, bl3_ccra, bl3_cit, bl3_cpha, bl3_gim, bl3_imp, bl3_1, bl3_shw, bl3_sim, bl3_vim, ble, blt, bmr, cara, cata10, cata11, cata12, cata13, cata14, cata15, cata16, cata1, cata2, cata3, cata4, cata5, cata6, cata7, cata8, cata9, catb1, catb2, catb3, catb4, catb5, ceoa, ceob, cml_e1, cml_e2, cml_e3, cml_e4, cml_e5, cml_e6, cml_e7, cml_e8, dfra10, dfra12, dfra13, dfra14, dfra15, dfra16, dfra17, dfra19, dfra1, dfra20, dfra21, dfra22, dfra23, dfra24, dfra25, dfra25, dfra25, dfra26, dfra5, dfra7, dfrb1, dfrb2, dfrb3, dfrb6, emea, emrd, emre, erea, ereb, erma, ermb, ermc, ermd, erme, ermf, ermg, ermh, ermn, ermo, ermq, ermr, erms, ermt, ermu, ermv, ermw, ermx, ermy, fosa, fosb, fosc, fosx, fusb, fush, ksga, lmra, lmrb, lnua, lnub, lsa, maca, macb, mdte, mdtf, mdtg, mdth, mdtk, mdtl, mdtm, mdtn, mdto, mdtp, meca, mecr1, mefa, mepa, mexa, mexb, mexc, mexd, mexe, mexf, mexh, mexi, mexw, mexx, mexy, mfpa, mpha, mphb, mphc, msra, norm, oleb, opcm, opra, oprd, oprj, oprm, oprn, otra, otrb, pbp1a, pbp1b, pbp2b, pbp2, pbp2x, pmra, qac, qaca, qacb, qnra, qnrb, qnrs, rosa, rosb, smea, smeb, smec, smed, smee, smef, srmb, sta, str, sul1, sul2, sul3, tcma, tcr3, tet30, tet31, tet32, tet33, tet34, tet36, tet37, tet38, tet39, tet40, teta, tetb, tetc, tetd, tete, tetg, teth, tetj, tetk, tetl, tetm, teto, tetpa, tetpb, tet, tetq, tets, tett, tetu, tetv, tetw, text, tety, tetz, tlrc, tmrb, tolc, tsnr, vana, vanb, vanc, vand, vane, vang, vanha, vanhb, vanhd, vanra, vanrb, vanrc, vanrd, vanre, vanrg, vansa, vansb, vansc, vansd, vanse, vansg, vant, vante, vantg, vanug, vanwb, vanwg, vanxa, vanxb, vanxd, vanxyc, vanxye, vanxyg, vanya, vanyb, vanyd, vanyg, vanz, vata, vatb, vatc, vatd, vate, vgaa, vgab, vgba, vgbb, vph, ykkc, and ykkd (see the Antibiotic Resistance Genes Database (ARDB) available online).

In certain embodiments, the method of the present invention further comprises treating the subject with an antibiotic or regime of antibiotics. Non-limiting examples of such antibiotics include amoxillin, erythromycin, azithromycin, clarithromycin, gentamicin, tobramycin, ciprofloxaxin, norfloxacin, gatifloxacin, ofloxacin, levofloxacin, moxifloxacin, metronidazole, lomefloxacin, ciprofloxacin, natamycin, neomycin, polymyxin B, gentamycin, bacitracin, trovafloxacin, grepafloxacin, sulfacetamide, tetracycline, gramicidin, chloramphenicol, or gramicidin.amino glycosides (gentamicin, neomycin, kanamycin, tobramycin, framycetin, streptomycin, amikacin), ampicillin and amoxillin, sulphonamides (trimethoprim-sulfamethoazole), cephalosporins, groups of beta-lactams, chloramphenicols, lincosamides, macrolides, penicillin, group of quinolones, tetracyclins and nitrafuratoin/nitrofurazone, polymyxin B, mupirocin, vancomycin, antimicrobial agents containing one or more biguanide groups (for example chlorhexidine or PHMB), silver complexes or silver salts, hydrogenperoxide and other oxidizing agents, quaternary ammonium compounds, agents delivering chlorine, and antimicrobial peptides.

In some embodiments, the nucleic acids from the sample is analyzed by Sequencing by Synthesis (SBS) techniques. SBS techniques generally involve the enzymatic extension of a nascent nucleic acid strand through the iterative addition of nucleotides against a template strand. In traditional methods of SBS, a single nucleotide monomer may be provided to a target nucleotide in the presence of a polymerase in each delivery. However, in some of the methods described herein, more than one type of nucleotide monomer can be provided to a target nucleic acid in the presence of a polymerase in a delivery.

SBS can utilize nucleotide monomers that have a terminator moiety or those that lack any terminator moieties. Methods utilizing nucleotide monomers lacking terminators include, for example, pyrosequencing and sequencing using γ-phosphate-labeled nucleotides. In methods using nucleotide monomers lacking terminators, the number of different nucleotides added in each cycle can be dependent upon the template sequence and the mode of nucleotide delivery. For SBS techniques that utilize nucleotide monomers having a terminator moiety, the terminator can be effectively irreversible under the sequencing conditions used as is the case for traditional Sanger sequencing which utilizes dideoxynucleotides, or the terminator can be reversible as is the case for sequencing methods developed by Solexa (now Illumina, Inc.). In preferred methods a terminator moiety can be reversibly terminating.

SBS techniques can utilize nucleotide monomers that have a label moiety or those that lack a label moiety. Accordingly, incorporation events can be detected based on a characteristic of the label, such as fluorescence of the label; a characteristic of the nucleotide monomer such as molecular weight or charge; a byproduct of incorporation of the nucleotide, such as release of pyrophosphate; or the like. In embodiments, where two or more different nucleotides are present in a sequencing reagent, the different nucleotides can be distinguishable from each other, or alternatively, the two or more different labels can be the indistinguishable under the detection techniques being used. For example, the different nucleotides present in a sequencing reagent can have different labels and they can be distinguished using appropriate optics as exemplified by the sequencing methods developed by Solexa (now Illumina, Inc.). However, it is also possible to use the same label for the two or more different nucleotides present in a sequencing reagent or to use detection optics that do not necessarily distinguish the different labels. Thus, in a doublet sequencing reagent having a mixture of A/C both the A and C can be labeled with the same fluorophore. Furthermore, when doublet delivery methods are used all of the different nucleotide monomers can have the same label or different labels can be used, for example, to distinguish one mixture of different nucleotide monomers from a second mixture of nucleotide monomers. For example, using the [First delivery nucleotide monomers]+[Second delivery nucleotide monomers] nomenclature set forth above and taking an example of A/C+(1/T), the A and C monomers can have the same first label and the G and T monomers can have the same second label, wherein the first label is different from the second label. Alternatively, the first label can be the same as the second label and incorporation events of the first delivery can be distinguished from incorporation events of the second delivery based on the temporal separation of cycles in an SBS protocol. Accordingly, a low resolution sequence representation obtained from such mixtures will be degenerate for two pairs of nucleotides (T/G, which is complementary to A and C, respectively; and C/A which is complementary to G/T, respectively).

Some embodiments include pyrosequencing techniques. Pyrosequencing detects the release of inorganic pyrophosphate (PPi) as particular nucleotides are incorporated into the nascent strand (Ronaghi, M., Karamohamed, S., Pettersson, B., Uhlen, M. and Nyren, P. (1996) "Real-time DNA sequencing using detection of pyrophosphate release." Analytical Biochemistry 242(1), 84-9; Ronaghi, M. (2001) "Pyrosequencing sheds light on DNA sequencing." Genome Res. 11(1), 3-11; Ronaghi, M., Uhlen, M. and Nyren, P. (1998) "A sequencing method based on real-time pyrophosphate." Science 281(5375), 363; U.S. Pat. Nos. 6,210,891; 6,258,568 and 6,274,320, the disclosures of which are incorporated herein by reference in their entireties). In pyrosequencing, released PPi can be detected by being immediately converted to adenosine triphosphate (ATP) by ATP sulfurylase, and the level of ATP generated is detected via luciferase-produced photons.

In another example type of SBS, cycle sequencing is accomplished by stepwise addition of reversible terminator nucleotides containing, for example, a cleavable or photobleachable dye label as described, for example, in U.S. Pat. Nos. 7,427,67, 7,414,1163 and 7,057,026, the disclosures of which are incorporated herein by reference. This approach is being commercialized by Solexa (now Illumina Inc.), and is also described in WO 91/06678 and WO 07/123,744 (filed in the United States Patent and Trademark Office as U.S. Ser. No. 12/295,337), each of which is incorporated herein by reference in their entireties. The availability of fluorescently-labeled terminators in which both the termination can be reversed and the fluorescent label cleaved facilitates efficient cyclic reversible termination (CRT) sequencing. Polymerases can also be co-engineered to efficiently incorporate and extend from these modified nucleotides.

In other embodiments, Ion Semiconductor Sequencing is utilized to analyze the nucleic acids from the sample. Ion Semiconductor Sequencing is a method of DNA sequencing based on the detection of hydrogen ions that are released during DNA amplification. This is a method of "sequencing by synthesis," during which a complementary strand is built based on the sequence of a template strand.

For example, a microwell containing a template DNA strand to be sequenced can be flooded with a single species of deoxyribonucleotide (dNTP). If the introduced dNTP is complementary to the leading template nucleotide it is incorporated into the growing complementary strand. This causes the release of a hydrogen ion that triggers a hypersensitive ion sensor, which indicates that a reaction has occurred. If homopolymer repeats are present in the template sequence multiple dNTP molecules will be incorporated in a single cycle. This leads to a corresponding number of released hydrogens and a proportionally higher electronic signal.

This technology differs from other sequencing technologies in that no modified nucleotides or optics are used. Ion semiconductor sequencing may also be referred to as ion torrent sequencing, proton-mediated sequencing, silicon sequencing, or semiconductor sequencing. Ion semiconductor sequencing was developed by Ion Torrent Systems Inc. and may be performed using a bench top machine. Rusk, N. (2011). "Torrents of Sequence," Nat Meth 8(1): 44-44. Although it is not necessary to understand the mechanism of an invention, it is believed that hydrogen ion release occurs during nucleic acid amplification because of the formation of a covalent bond and the release of pyrophosphate and a charged hydrogen ion. Ion semiconductor sequencing exploits these facts by determining if a hydrogen ion is released upon providing a single species of dNTP to the reaction.

For example, microwells on a semiconductor chip that each contain one single-stranded template DNA molecule to be sequenced and one DNA polymerase can be sequentially flooded with unmodified A, C, G or T dNTP. Pennisi, E. (2010). "Semiconductors inspire new sequencing technologies" Science 327(5970): 1190; and Perkel, J., "Making contact with sequencing's fourth generation" Biotechniques (2011). The hydrogen ion that is released in the reaction changes the pH of the solution, which is detected by a hypersensitive ion sensor. The unattached dNTP molecules are washed out before the next cycle when a different dNTP species is introduced.

Beneath the layer of microwells is an ion sensitive layer, below which is a hypersensitive ISFET ion sensor. All layers are contained within a CMOS semiconductor chip, similar to that used in the electronics industry. Each released hydrogen ion triggers the ISFET ion sensor. The series of electrical pulses transmitted from the chip to a computer is translated into a DNA sequence, with no intermediate signal conversion required. Each chip contains an array of microwells with corresponding ISFET detectors. Because nucleotide incorporation events are measured directly by electronics, the use of labeled nucleotides and optical measurements are avoided.

An example of a Ion Semiconductor Sequencing technique suitable for use in the methods of the provided disclosure is Ion Torrent sequencing (U.S. Patent Application Numbers 2009/0026082, 2009/0127589, 2010/0035252, 2010/0137143, 2010/0188073, 2010/0197507, 2010/0282617, 2010/0300559), 2010/0300895, 2010/0301398, and 2010/0304982), the content of each of which is incorporated by reference herein in its entirety. In Ion Torrent sequencing, DNA is sheared into fragments of approximately 300-800 base pairs, and the fragments are blunt ended. Oligonucleotide adaptors are then ligated to the ends of the fragments. The adaptors serve as primers for amplification and sequencing of the fragments. The fragments can be attached to a surface and are attached at a resolution such that the fragments are individually resolvable. Addition of one or more nucleotides releases a proton (H+), which signal detected and recorded in a sequencing instrument. The signal strength is proportional to the number of nucleotides incorporated. User guides describe in detail the Ion Torrent protocol(s) that are suitable for use in methods of the invention, such as Life Technologies' literature entitled "Ion Sequencing Kit for User Guide v. 2.0" for use with their sequencing platform the Personal Genome Machine™ (PCG).

In some embodiments, as a part of the sample preparation process, "barcodes" may be associated with each sample. In this process, short oligos are added to primers, where each different sample uses a different oligo in addition to a primer.

The term "library", as used herein refers to a library of genome-derived sequences. The library may also have sequences allowing amplification of the "library" by the polymerase chain reaction or other in vitro amplification methods well known to those skilled in the art. The library may also have sequences that are compatible with next-generation high throughput sequencers such as an ion semiconductor sequencing platform.

In certain embodiments, the primers and barcodes are ligated to each sample as part of the library generation process. Thus during the amplification process associated with generating the ion amplicon library, the primer and the short oligo are also amplified. As the association of the barcode is done as part of the library preparation process, it is possible to use more than one library, and thus more than one sample. Synthetic DNA barcodes may be included as part of the primer, where a different synthetic DNA barcode may be used for each library. In some embodiments, different libraries may be mixed as they are introduced to a flow cell, and the identity of each sample may be determined as part of the sequencing process. Sample separation methods can be used in conjunction with sample identifiers. For example a chip could have 4 separate channels and use 4 different barcodes to allow the simultaneous running of 16 different samples.

The present invention is further illustrated by the following examples that should not be construed as limiting. The contents of all references, patents, and published patent applications cited throughout this application, as well as the Figures, are incorporated herein by reference in their entirety for all purposes.

EXAMPLES

Example 1

*Mycobacterium tuberculosis* (Mtb) Heteroresistance Assay Optimization and Validation The goal of this study was to detect and quantify the presence of resistant alleles associated with primary TB drug (INH, RIF, MOX, AMK, KAN, and CAP) resistance that occur in ≤0.1% of a mixed (resistant/susceptible) population of Mtb in clinical samples. To accomplish this goal the Inventors optimized and validated a prototype Mtb heteroresistance assay based on NGS technology, which can accurately detect resistant alleles (minor components) down to less than 0.1%, for all known SNPs associated with XDR-TB in six primary resistance genes.

The Inventors exploited the deep-sequencing capability of the Illumina NGS platforms to detect extremely rare minor components in an Mtb population. The deep-sequencing coverage capacity is dependent on the complexity of the genomic material being sequenced; in the case of resistance in Mtb the Inventors focused on sequencing amplicons (~300 bp) that contain drug resistance target loci: SNPs previously demonstrated to predict XDR-TB phenotypic resistance with 90-98% sensitivity and ~100% specificity. This short genomic length allows for $10^4 \times$-$10^5 \times$ coverage for each individual amplicon, for all target resistance gene regions, for up to 100 distinct clinical samples on a single Illumina MiSeq run. However, as stated above, the lower limit of detection for each targeted loci is directly related to the sequencing error rate, not the coverage. The Inventors advanced the ability to detect extremely rare SNP alleles below the error rate using high fidelity Taq polymerase, improved alignment algorithms, advanced bioinformatics, and minor variant analysis. The use of high fidelity thermostable polymerases reduces the impact of PCR-amplification error on minor variant detection. The error rate of KAPA HiFi ($2.8 \times 10^{-7}$) is 100× lower than Taq polymerase and 40× lower than polymerase blends such as PLATINUM® Taq High Fidelity. Improvements in alignment algorithms have allowed for more accurate assemblies and alignments of sequence data, which result in the reduction of the overall error rate. Advanced bioinformatics tools, developed in house, better handle the extreme sequence coverage (>100,000×), allowing for the detection of ultra-rare variants.

The most significant advance in minor variant detection has come from "haplotype variant analysis", which involves the detection and quantitation of multiple independent variant loci. In short, haplotype variant analysis predicts that the lower limit of minor component detection decreases by the product of individual error rates for the number of target loci contained in an individual sequence read (Box 1). Therefore, if only one SNP loci is interrogated and that loci has a known sequencing error rate of $10^{-3}$ (0.1%), then the theoretical lower limit of detection (LOD) is $>10^{-3}$ and is greatly influenced by the sequence coverage. However, if two separate SNP loci are interrogated on a single read, each of which has a sequencing error of $10^{-3}$, then their haplotype combined error rate is the product of the individual error rates, or $10^{-6}$; for the sake of a simplified probabilistic discussion (Box 1), a conservative LOD that is 10-fold higher or $10^{-5}$ (0.001%) is used. The Inventors used this product rule of probability characteristic of haplotype variant analysis to establish a deep-sequencing count-based rare-variant detection assay for forensic analyses using highly controlled mixtures of synthetic plasmids and well characterized *Bacillus anthracis* genomic material. As long as the sequence of the target genomes and all the SNP loci are well understood, it is relatively easy to identify regions with di-nucleotide or even tri-nucleotide haplotypes to target for minor variant sequence analysis.

Box 1. The Effect of Haplotype Analysis on Detection of Minor Variants

LOD = ($X^n$)(10)(100)
L = the lower limit (%) of minor variant detection
X = the average sequence error rate, and
n = the number of target SNP loci on a single sequencing read In order to establish such an assay for Mtb, the Inventors adapted the haplotype accuracy and sensitivity to Mtb resistance markers. Unfortunately, this haplotype approach is only applicable to SNP loci that can be detected on a single sequencing read. As most resistance mechanisms in Mtb are due to SNP loci in several different genomically dispersed genes, it is not possible to generate a di-nucleotide haplotype for every targeted resistance loci within a single sequencing read. To overcome this, the Inventors established a conceptually similar approach of "Single Molecule with Overlapping Reads" (SMOR) analysis for individual targeted SNP loci. With SMOR, the Inventors exploited the most recent advances in NGS technology by using longer over-lapping paired end sequence reads to interrogate single loci twice in linked sequencing reads. The Illumina MiSeq platform may be used with 300 bp paired end sequencing chemistry, which results in nearly complete overlap of the forward and reverse reads at target loci. This allows for effective coverage of each locus on both strands of an individual sequenced DNA molecule, which in turn allows for an independent confirmation of the specific nucleotide at that single locus. A similar approach of independently tagging each strand and sequencing separately has been validated; however, the approach here is to sequence both strands consecutively. Again, the product rule of probability applies, such that if one locus on a single molecule is read two times, it has the same lower limit of detection as a haplotype of two distinct loci on one read. Therefore, if a particular SNP locus has a sequencing error rate of 0.25% (typical for a high GC genome such as Mtb on Illumina technology), the limit of accurate detection may be LOD= $(0.0025^2)(10)(100)=0.006\%$ with the present invention.

Figure 2:
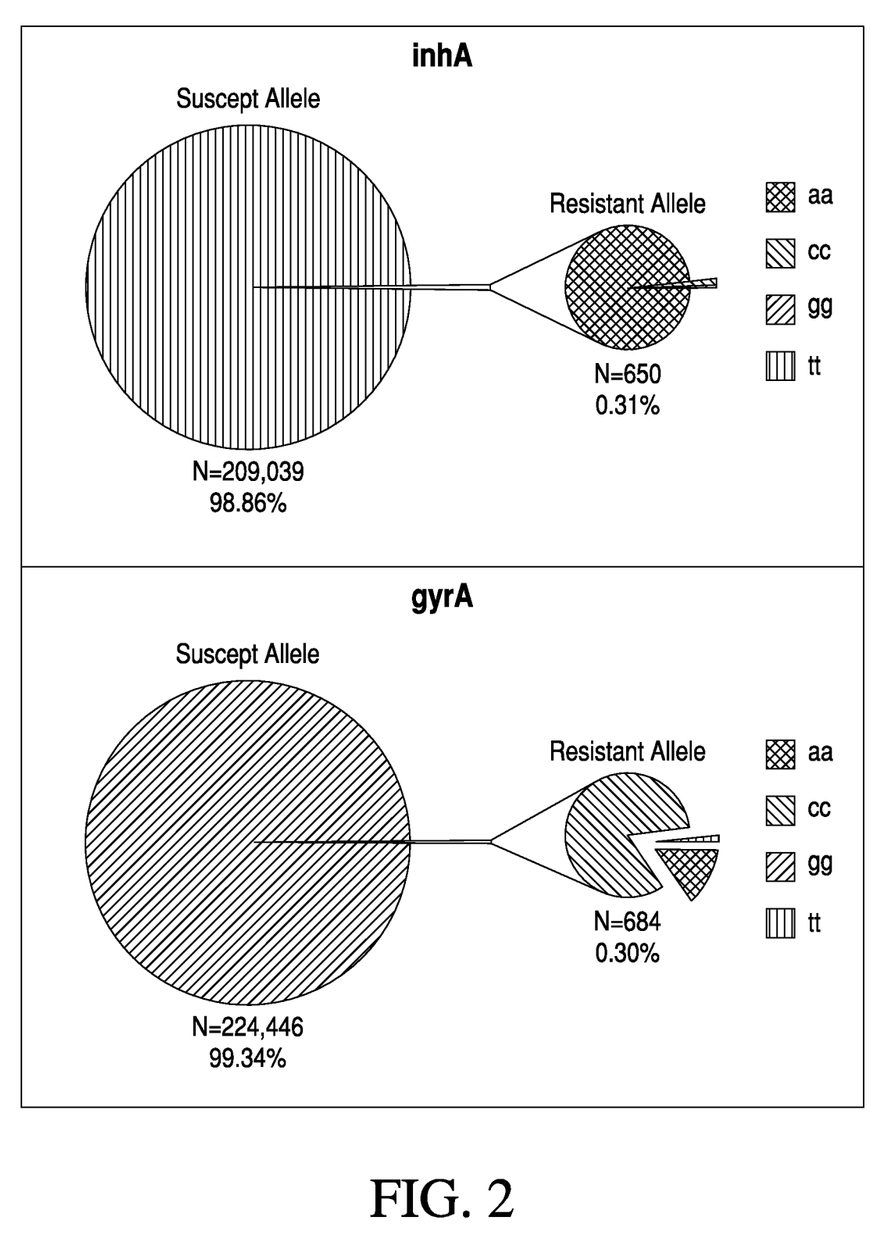
FIG. 2 depicts SMOR analysis of reads for inhA and gyrA.

FIG. 2 shows the number of paired complimentary strand reads for resistance-conferring SNPs in the gyrA and inhA genes in experimentally derived mixtures of "pure" susceptible and "pure" resistant Mtb genomes at approximately 999:1 (~0.3%), respectively. An analysis was conducted on a number of resistance genes (rrs, katG, inhA, and gyrA), providing ample evidence for the proof of principle for this assay. Sequencing error is readily detected and is easily separated from "true calls".

Figure 3:
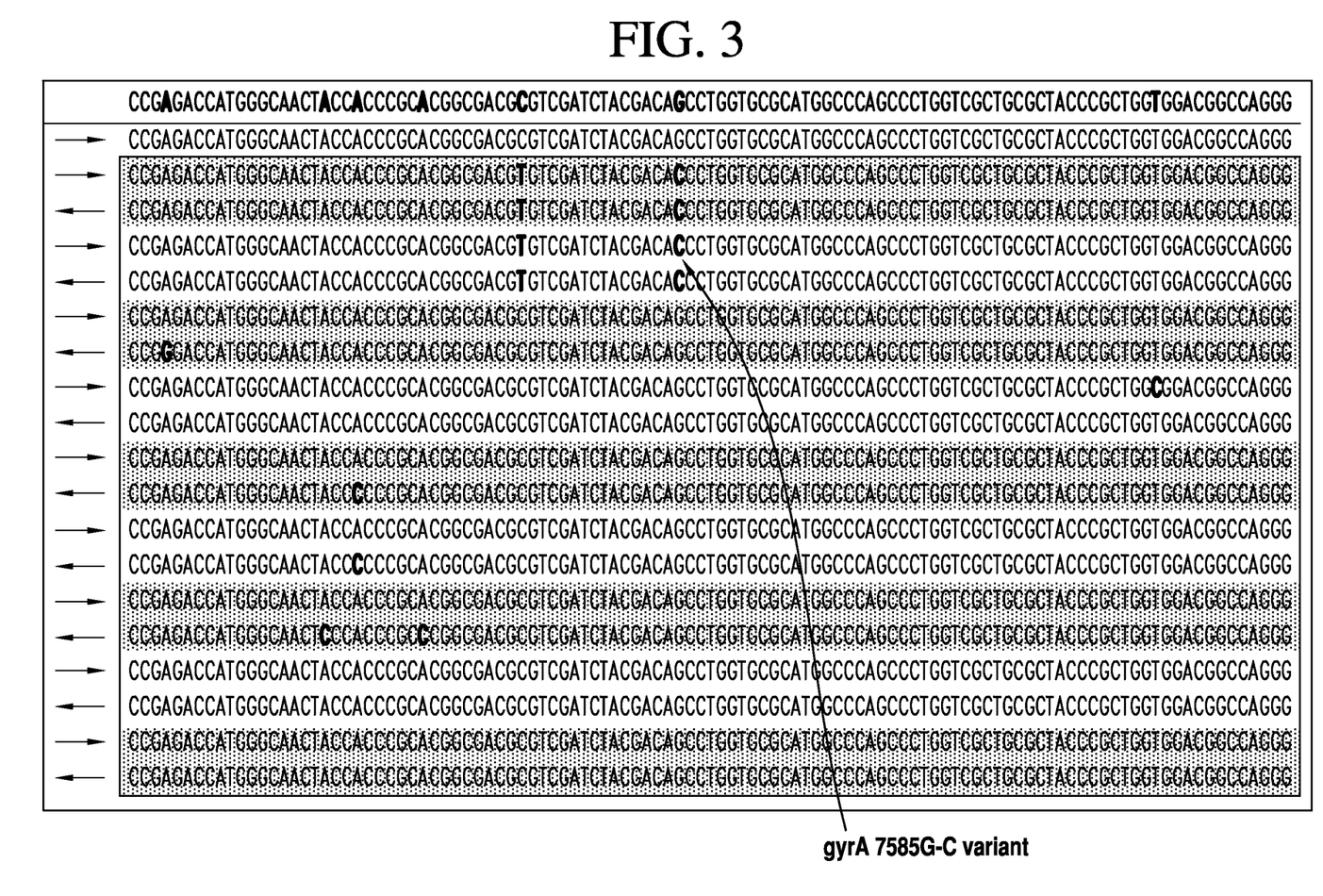
FIG. 3 depicts mixed read alignment to gyrA from overlapping read analysis with six different sequences shown (SEQ ID NOs: 1-6). A mixture of resistant (1%) and susceptible (99%) alleles was sequenced to >224,000× coverage and the alignment of 18 reads (9 paired sets) is shown to illustrate the detection of minor variants. Random single SNPs occurring on one strand but not their complement are distinguished from real variants (two examples) as sequencing errors.

FIG. 3 is a visualization of actual paired overlapping reads aligned to the gyrA sequence, from a 99:1 susceptible to resistant mixture (1%), showing the presence of resistance allele and susceptible allele states (shading denotes sequences from paired reads).

Heteroresistance Detection Assay (HDA) Optimization

The Inventors devised a strategy to identify single resistance conferring mutations down to 0.1% or less using the Illumina MiSeq tabletop sequencer, by making use of SMOR analysis. This strategy may be used in an assay for 36 markers on six resistance-associated genes: katG, inhA promoter, rpoB, gyrA, rrs, eis promoter. Current MiSeq throughput allows for up to 96 patient samples (with up to 6 target genes) in a single run and still obtain $>10^5$ reads per target, allowing for variant detection to less than 0.1% (LOD~$10^{-4}$), if present. The final assay included a Mtb-specific quantitative PCR analysis of each clinical sample to establish quantity of Mtb present in the sample.

HDA Standards

The assay may include a highly homogeneous synthetic plasmid DNA standard that contains each well-described resistance conferring mutation, for up to 6 genes (~36 SNPs). Deep sequencing of the standard enables identification of actual sequence error rate variance between loci and sequencing runs. The standards are used as error controls for the HDA assays.

HDA Validation

A two-pronged approach is used to validate the HDA: 1) Applying the HDA to known mixtures of pan-susceptible and pan-resistant strains, to assess the assay's accuracy and level of detection for each target; 2) Validate its ability to accurately detect minor variant in clinical samples using normal flora sputum spiked with target DNA, to assess impact of human and background microbial DNA on assay performance.

Example 2

Heteroresistance Analysis of Clinical Tuberculosis Patient Specimens

The premise of this study was that Mtb heteroresistance can be detected in patient samples prior to treatment failure. Dynamic changes can be quantified in Mtb populations and heterogeneity found in serial clinical specimens in order to track the population dynamics of pre-existing or emergent resistant sub-populations and to determine at what level sub-populations of resistant organisms of the total Mtb population predict acquired drug resistance and poor treatment outcomes.

The goal was to quantify dynamic changes in Mtb heteroresistance to isoniazid (INH), rifampin (RIF), moxifloxacin (MOX), amikacin (AMK), kanamycin (KAN) and/or capreomycin (CAP) in a prospective study of tuberculosis (TB) and drug-resistant tuberculosis (DR-TB) patients through the first nine months of their treatment or retreatment. The Inventors wanted to determine if the presence and/or expansion of minor variant Mtb subpopulations with resistant alleles are associated with poor clinical outcomes such as time to sputum and culture conversion and clinical improvement.

The project leverages the existing NIH-sponsored Global Consortium for Drug-resistant TB Diagnostics (GCDD) clinical study results and infrastructure. The Inventors' group (GCDD) completed whole genome sequencing analysis of over 400 clinical multi/extensively drug resistant tuberculosis (M/XDR-TB) isolates from India, Moldova, Philippines and South Africa to quantifying the sensitivity and specificity of individual SNPs and groups of SNPs as markers of clinically relevant phenotypic resistance. Based on this work, the Inventors determined that detection of 30-50 specific SNPs in six genes (katG, inhA promoter, rpoB, gyrA, rrs and eis promoter) detects 90-98% of Mtb isolates with clinically relevant phenotypic resistance to INH, RIF, FQ, AMK, KAN and CAP with almost 100% specificity. The GCDD global infrastructure has validated fluorescent smear microscopy, tuberculosis identification, MGIT DST (1st and 2nd line drugs), and DNA extraction (used for line probe assays and pyrosequencing) at the Phthisis Pneumology Institute Laboratory (Chisinau, Moldova), along with clinical sites in Mumbai, India and Port Elizabeth, South Africa. The Inventors enrolled 225 study participants in Moldova, 586 in India, and 275 in South Africa, all suspected of having MDR-TB, into a study focused on reducing the time of detection of XDR-TB from months to one week.

Heteroresistance Analysis

Figure 4:
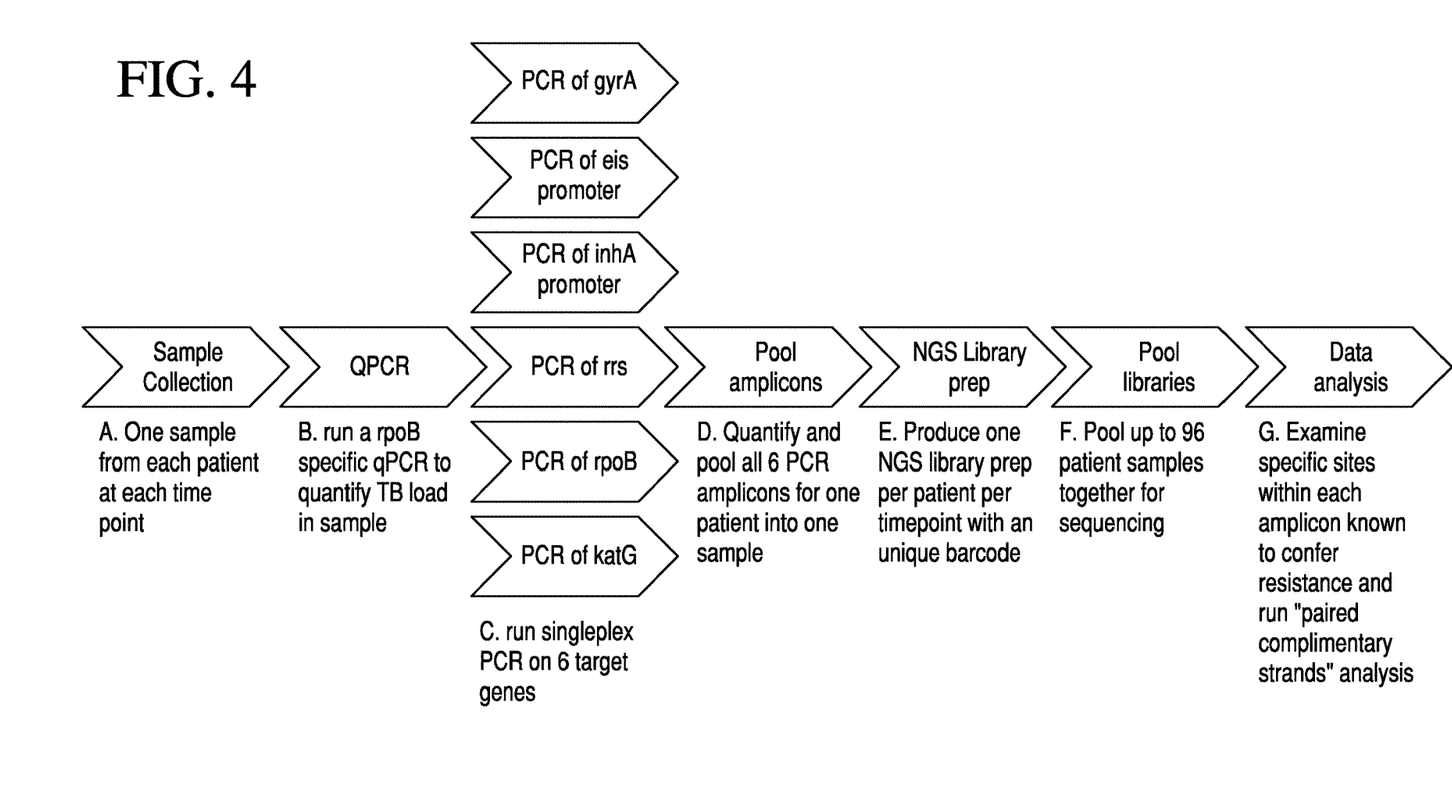
FIG. 4 depicts a sample analysis pipeline with a SMOR heteroresistance detection assay.

A sample analysis pipeline was established (FIG. 4). Briefly: (A) Sample collection and extraction are accomplished with standard methods; (B) qPCR is run targeting the single copy rpoB gene, to establish a limit of detection for each sample based on the actual quantity of genomes per sample; (C) Six gene regions of the Mtb genome (katG, inhA promoter, rpoB, gyrA, rrs, eis promoter; all of which contain the 42 different resistance-conferring SNP loci, are amplified using hi-fidelity polymerase; (D) All six amplicons are pooled together for each patient at each time point in equal molar concentration; (E) A single next-generation sequencing Illumina library preparation is made for each amplicon pool; (F) Several different NGS libraries (up to 96) are pooled together in equal molar concentration for sequencing on the MiSeq (a plasmid control is sequenced with every sequencing pool to examine error of individual runs on the sequencing instrument); and (G) A bioinformatic analysis is conducted of all target loci, and the ratio of non-resistant to resistant allele states is quantified using in-house developed and publically available scripts including SMOR analysis.

The contents of all references, patents, and published patent applications cited throughout this application, as well as the Figures, are incorporated herein by reference in their entirety for all purposes.

Unless defined otherwise, all technical and scientific terms herein have the same meaning as commonly understood by one of ordinary skill in the art to which this invention belongs. Although any methods and materials, similar or equivalent to those described herein, can be used in the practice or testing of the present invention, the preferred methods and materials are described herein. All publications, patents, and patent publications cited are incorporated by reference herein in their entirety for all purposes.

The publications discussed herein are provided solely for their disclosure prior to the filing date of the present application. Nothing herein is to be construed as an admission that the present invention is not entitled to antedate such publication by virtue of prior invention.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

REFERENCES

So as to reduce the complexity and length of the Detailed Specification, the Inventors herein expressly incorporate by reference to the extent applicable, all of the following materials.

Adjers-Koskela K, Katila M L. Susceptibility testing with the manual mycobacteria growth indicator tube (MGIT) and the MGIT 960 system provides rapid and reliable verification of multidrug-resistant tuberculosis. J Clin Microbiol. 2003; 41(3):1235-9.

Ajbani K, Nikam C, Kazi M, Gray C, Boehme C, Balan K, Shetty A, Rodrigues C. Evaluation of genotype MTBDRsl assay to detect drug resistance associated with fluoroquinolones, aminoglycosides and ethambutol on clinical sediments. PLoS One. 2012; 7(11): e49433.

Beauchemin C A, McSharry J J, Drusano G L, Nguyen J T, Went G T, Ribeiro R M, et al. Modeling amantadine treatment of influenza A virus in vitro. J Theor Biol. 2008; 254(2):439-51. PMCID: 2663526.

CDC. FluView: 2009-2010 Influenza Season: Week 50 ending Dec. 19, 2009. http://wwwcdcgov/flu/weekly/.2009.

Centers for Disease Control and Prevention. Oseltamivir-resistant novel influenza A (H1N1) virus infection in two immunosuppressed patients—Seattle, Wash., 2009. MMWR Morb Mortal Wkly Rep. 2009; 58(32): 893-6.

Chen-Harris H, Borucki M K, Torres C, Slezak T R, Allen J E. Ultra-deep mutant spectrum profiling: improving sequencing accuracy using overlapping read pairs. BMC Genomics. 2013; 14:96. PMCID: 3599684.

Colijn C, Cohen T, Ganesh A, Murray M. Spontaneous emergence of multiple drug resistance in tuberculosis before and during therapy. PLoS One. 2011; 6(3): e18327.

Colman R E S J, Smith D, Gillece J, Rawat A, Usher J, Engelthaler D M, Foster J, Keim P. Haplotype analysis for Bacterial Rare Variant Detection. 11th Annual ASM Biodefense and Emerging Diseases Research Meeting; Feb. 25-27, 2013; Washington D.C. 2013.

Colman R E, Schupp J A, Smith D, Keim P S, Valafar F, Rodwell T C, et al. Advancing heteroresistance detection in tuberculosis using single-molecule-overlapping read (SMOR) analysis. IDSA Conference, San Francisco, Calif., October 2013. 2013.

Cullen M M, Sam N E, Kanduma E G, McHugh T D, Gillespie S H. Direct detection of heteroresistance in *Mycobacterium tuberculosis* using molecular techniques. J Med Microbiol. 2006; 55(Pt 8):1157-8.

Cushing A, Flaherty P, Hopmans E, Bell J M, Ji H P. RVD: a command-line program for ultrasensitive rare single nucleotide variant detection using targeted next-generation DNA resequencing. BMC Research Notes. 2013; 6(1):206.

Duwe S, Schweiger B. A new and rapid genotypic assay for the detection of neuraminidase inhibitor resistant influenza A viruses of subtype H1N1, H3N2, and H5N1. Journal of virological methods. 2008; 153(2): 134-41.

Ellebedy A H, Webby R J. Influenza vaccines. Vaccine. 2009; 27 Suppl 4:D65-8.

Flaherty P, Natsoulis G, Muralidharan O, Winters M, Buenrostro J, Bell J, Brown S, Holodniy M, Zhang N, Ji H P. Ultrasensitive detection of rare mutations using next-generation targeted resequencing. Nucleic Acids Res. 2012; 40(1):e2.

Folkvardsen D B, Svensson E, Thomsen V O, Rasmussen E M, Bang D, Werngren J, Hoffner S, Hillemann D, Rigouts L. Can molecular methods detect 1% isoniazid resistance in *Mycobacterium tuberculosis*?J Clin Microbiol. 2013; 51(5):1596-9.

Fordyce S L, Bragstad K, Pedersen S S, Jensen T G, Gahrn-Hansen B, Daniels R, et al. Genetic diversity among pandemic 2009 influenza viruses isolated from a transmission chain. Virol J. 2013; 10:116. PMCID: 3639878.

Gandhi N R, Nunn P, Dheda K, Schaaf H S, Zignol M, van Soolingen D, Jensen P, Bayona J. Multidrug-resistant and extensively drug-resistant tuberculosis: a threat to global control of tuberculosis. Lancet. 2010; 375 (9728): 1830-43.

Gillespie S H. Evolution of drug resistance in *Mycobacterium tuberculosis*: clinical and molecular perspective. Antimicrob Agents Chemother. 2002; 46(2):267-74.

Hayden F. Developing new antiviral agents for influenza treatment: what does the future hold?Clin Infect Dis. 2009; 48 Suppl 1:S3-S13.

Hoopes J D, Driebe E M, Kelley E, Engelthaler D M, Keim P S, Perelson A S, et al. Triple combination antiviral drug (TCAD) composed of amantadine, oseltamivir, and ribavirin impedes the selection of drug-resistant influenza A virus. PLoS One. 2011; 6(12): e29778. PMCID: 3248427.

Huse S M, Huber J A, Morrison H G, Sogin M L, Welch D. Accuracy and quality of massively parallel DNA pyrosequencing. Genome Biology. 2007; 8(7):R143.

Jonsson G, Furin J. Will molecular diagnosis of drug-resistant tuberculosis improve patient outcomes?Int J Tuberc Lung Dis. 2012; 16(1):4-5.

Kampmann M L, Fordyce S L, Avila-Arcos M C, Rasmussen M, Willerslev E, Nielsen L P, et al. A simple method for the parallel deep sequencing of full influenza A genomes. J Virol Methods. 2011; 178(1-2):243-8.

Karahan Z C, Akar N. Restriction endonuclease analysis as a solution for determining rifampin resistance mutations by automated DNA sequencing in heteroresistant *Mycobacterium tuberculosis* strains. Microbial drug resistance. 2005; 11(2): 137-40.

Kunisaki K M, Janoff E N. Influenza in immunosuppressed populations: a review of infection frequency, morbidity, mortality, and vaccine responses. Lancet Infect Dis. 2009; 9(8):493-504.

Larder B A, Kohli A, Kellam P, Kemp S D, Kronick M, Henfrey R D. Quantitative detection of HIV-1 drug resistance mutations by automated DNA sequencing. Nature. 1993; 365(6447):671-3.

Lee N, Chan P K, Hui D S, Rainer T H, Wong E, Choi K W, et al. Viral loads and duration of viral shedding in adult patients hospitalized with influenza. J Infect Dis. 2009; 200(4):492-500.

Lipsitch M, Levin B R. Population dynamics of tuberculosis treatment: mathematical models of the roles of non-compliance and bacterial heterogeneity in the evolution of drug resistance. The international journal of tuberculosis and lung disease: the official journal of the International Union against Tuberculosis and Lung Disease. 1998; 2(3):187-99.

Liu C M, Driebe E M, Schupp J, Kelley E, Nguyen J T, McSharry J J, et al. Rapid quantification of single-nucleotide mutations in mixed influenza A viral populations using allele-specific mixture analysis. J Virol Methods. 2010; 163(1): 109-15.

Long Q, Jeffares D C, Zhang Q, Ye K, Nizhynska V, Ning Z, Tyler-Smith C, Nordborg M. PoolHap: inferring haplotype frequencies from pooled samples by next generation sequencing. PLoS One. 2011; 6(1):e15292.

McCullers J A, Saito T, Iverson A R. Multiple Genotypes of Influenza B Virus Circulated between 1979 and 2003. Journal of Virology. 2004; 78(23): 12817-28.

Migliori G B, De Iaco G, Besozzi G, Centis R, Cirillo D M. First tuberculosis cases in Italy resistant to all tested drugs. Euro Surveill. 2007; 12(5).

Molinari N A, Ortega-Sanchez I R, Messonnier M L, Thompson W W, Wortley P M, Weintraub E, et al. The annual impact of seasonal influenza in the US: measuring disease burden and costs. Vaccine. 2007; 25(27): 5086-96.

Morandi L, de Biase D, Visani M, Cesari V, De Maglio G, Pizzolitto S, Pession A, Tallini G. Allele specific locked nucleic acid quantitative PCR (ASLNAqPCR): an accurate and cost-effective assay to diagnose and quantify KRAS and BRAF mutation. PLoS One. 2012; 7(4):e36084.

Nakamura K, Oshima T, Morimoto T, Ikeda S, Yoshikawa H, Shiwa Y, et al. Sequence-specific error profile of Illumina sequencers. Nucleic Acids Research. 2011; 39(13):e90-e.

Nguyen J T, Hoopes J D, Le M H, Smee D F, Patick A K, Faix D J, et al. Triple combination of amantadine, ribavirin, and oseltamivir is highly active and synergistic against drug resistant influenza virus strains in vitro. PLoS One. 2010; 5(2):e9332.

Nguyen J T, Hoopes J D, Smee D F, Prichard M N, Driebe E M, Engelthaler D M, et al. Triple combination of oseltamivir, amantadine, and ribavirin displays synergistic activity against multiple influenza virus strains in vitro. Antimicrob Agents Chemother. 2009; 53(10): 4115-26.

Nguyen J T, Smee D F, Barnard D L, Julander J G, Gross M, de Jong M D, et al. Efficacy of combined therapy with amantadine, oseltamivir, and ribavirin in vivo against susceptible and amantadine-resistant influenza A viruses. PLoS One. 2012; 7(1):e31006. PMCID: 3264642.

Organization W H. Policy guidance on drug-susceptibility testing (DST) of second-line antituberculosis drugs. World Health Organization, Geneva, Switzerland. 2008.

Rinder H, Mieskes K T, Loscher T. Heteroresistance in *Mycobacterium tuberculosis*. Int J Tuberc Lung Dis. 2001; 5(4):339-45.

Rinder H. Hetero-resistance: an under-recognised confounder in diagnosis and therapy?J Med Microbiol. 2001; 50(12):1018-20.

Rutvisuttinunt W, Chinnawirotpisan P, Simasathien S, Shrestha S K, Yoon I-K, Klungthong C, et al. Simultaneous and complete genome sequencing of Influenza A and B with high coverage by Illumina MiSeq Platform. Journal of Virological Methods. 2013.

Saunders N J, Trivedi U H, Thomson M L, Doig C, Laurenson I F, Blaxter M L. Deep resequencing of serial sputum isolates of *Mycobacterium tuberculosis* during therapeutic failure due to poor compliance reveals stepwise mutation of key resistance genes on an otherwise stable genetic background. J Infect. 2011; 62(3):212-7.

Schmitt M W, Kennedy S R, Salk J J, Fox E J, Hiatt J B, Loeb L A. Detection of ultra-rare mutations by next-generation sequencing. Proceedings of the National Academy of Sciences of the United States of America. 2012; 109(36): 14508-13.

Seo S, Englund J A, Nguyen J T, Pukrittayakamee S, Lindegardh N, Taming J, et al. Combination therapy with amantadine, oseltamivir and ribavirin for influenza A infection: safety and pharmacokinetics. Antivir Ther. 2013; 18(3):377-86.

Shah N S, Richardson J, Moodley P, Moodley S, Babaria P, Ramtahal M, Heysell S K, Li X, Moll A P, Friedland G, Sturm A W, Gandhi N R. Increasing drug resistance in extensively drug-resistant tuberculosis, South Africa. Emerging Infect Dis. 2011; 17(3):510-3.

Shendure J, Ji H. Next-generation DNA sequencing. Nature Biotechnology. 2008; 26(10): 1135-45.

Streicher E M, Bergval I, Dheda K, Bottger E C, Gey van Pittius N C, Bosman M, Coetzee G, Anthony R M, van Helden P D, Victor T C, Warren R M. *Mycobacterium tuberculosis* population structure determines the outcome of genetics-based second-line drug resistance testing. Antimicrobial agents and chemotherapy. 2012; 56(5):2420-7.

Sundstrom M, Edlund K, Lindell M, Glimelius B, Birgisson H, Micke P, Botling J. KRAS analysis in colorectal carcinoma: analytical aspects of Pyrosequencing and allele-specific PCR in clinical practice. BMC Cancer. 2010; 10:660.

Tolani M P, D'Souza D T, Mistry N F. Drug resistance mutations and heteroresistance detected using the GenoType MTBDRplus assay and their implication for treatment outcomes in patients from Mumbai, India. BMC Infect Dis. 2012; 12:9.

Udwadia Z F, Amale R A, Ajbani K K, Rodrigues C. Totally drug-resistant tuberculosis in India. Clin Infect Dis. 2012; 54(4):579-81.

Velayati A A, Masjedi M R, Farnia P, Tabarsi P, Ghanavi J, Ziazarifi A H, Hoffner S E. Emergence of new forms of totally drug-resistant tuberculosis bacilli: super extensively drug-resistant tuberculosis or totally drug-resistant strains in iran. Chest. 2009; 136(2):420-5.

Watson S J, Welkers M R, Depledge D P, Coulter E, Breuer J M, de Jong M D, et al. Viral population analysis and minority-variant detection using short read next-generation sequencing. Philos Trans R Soc Lond B Biol Sci. 2013; 368(1614):20120205. PMCID: 3678329.

Woods G L, Brown-Elliott B, Desmond E P, Hall G S, Heifets L, Pfyffer G E, Ridderhof J C, Wallace Jr R J, Warren N G, Witebsky F G. Susceptibility testing of mycobacteria, nocardiae, and other aerobic actinomycetes: approved standard: NCCLS; 2003.

Zhang X, Zhao B, Liu L, Zhu Y, Zhao Y, Jin Q. Subpopulation analysis of heteroresistance to fluoroquinolone in *Mycobacterium tuberculosis* isolates from Beijing, China. J Clin Microbiol. 2012; 50(4):1471-4.

(WHO) WHO. Global tuberculosis control 2011.

(WHO) WHO. Multidrug and extensively drug-resistant TB (M/XDR-TB): 2010 global report on surveillance and response.

What is claimed is:

1. A method of detecting a drug-resistant subpopulation within a heteroresistant population of a pathogen in a sample, the method comprising:
   a) providing a sample comprising a population of the pathogen;
   b) extracting nucleic acids from the sample;
   c) amplifying a target locus of the genome of the pathogen in the extracted nucleic acids to generate paired overlapping nucleic acid strands from a single DNA molecule, wherein the target locus comprises a region of interest comprising at least one minor variant associated with drug resistance of the drug-resistant subpopulation in the pathogen and each of the paired overlapping nucleic acid strands comprise the region of interest;
   d) consecutively sequencing the paired overlapping nucleic acid strands amplified from the same single DNA molecule of the target locus on a Next Generation Sequencing (NGS) platform to interrogate the region of interest of the single DNA molecule resulting in paired overlapping reads for the at least one minor variant;
   e) applying an alignment algorithm to sequencing data from the paired overlapping nucleic acid strands; and
   f) performing an analysis of the aligned sequencing data to detect the at least one minor variant, wherein the at least one minor variant is detected when present in the paired overlapping reads from the paired overlapping nucleic acid strands.

2. The method of claim 1, wherein the analysis of the aligned sequencing data is a minor variant analysis.

3. The method of claim 2, wherein the minor variant analysis is a haplotype variant analysis.

4. The method of claim 1, having a limit of detecting the at least one minor variant at less than about 0.1% of the heteroresistant population.

5. The method of claim 1, wherein the target locus is amplified with a high-fidelity polymerase.

6. The method of claim 1, wherein each of the overlapping nucleic acid strands consists of less than about 300 nucleotides.

7. The method of claim 1, wherein the alignment algorithm is optimized for short nucleotide space reads of less than about 300 nucleotides.

8. The method of claim 1, having a limit of detecting the at least one minor variant at less than about 0.05% of the heteroresistant population.

9. The method of claim 1, wherein the at least one minor variant occurs on both overlapping nucleic acid strands.

10. The method of claim 1, wherein the minor variant analysis is performed with a bioinformatics script that requires a user to input genomic regions of interest and generates a report with single molecule-overlapping read information used to identify the minor variant.

11. The method of claim 1, further comprising identifying actual sequence error rate variance between target loci and sequencing runs using a highly homogenous synthetic plasmid standard as a control.

12. The method of claim 1, wherein the minor variant is selected from the group consisting of: a single nucleotide polymorphism (SNP), an insertion, and a deletion.

13. The method of claim 1, wherein the pathogen is *Mycobacterium tuberculosis*.

14. The method of claim 13, wherein the at least one minor variant is located within a genomic sequence selected from the group consisting of: katG, inhA promoter, rpoB, gyrA, rrs, eis promoter, and combinations thereof.

15. The method of claim 13, wherein the drug-resistant subpopulation within the heteroresistant population of *M. tuberculosis* is resistant to isoniazid (INH), rifampin (RIF), moxifloxacin (MOX), amikacin (AMK), kanamycin (KAN) and/or capreomycin (CAP).

16. The method of claim 13, further comprising administering a therapeutic agent to the heteroresistant population of *M. tuberculosis*, wherein the therapeutic agent is selected from the group consisting of: PA-824, OPC-67683, SQ109, TMC207, NAS-21, NAS-91, thioridazine, chlorpromazine, 1,3-benzothiazin-4-one, and combinations thereof.

* * * * *

SEQUENCE LISTING

<160> NUMBER OF SEQ ID NOS: 6

<210> SEQ ID NO 1
<211> LENGTH: 109
<212> TYPE: DNA
<213> ORGANISM: Mycobacterium tuberculosis

<400> SEQUENCE: 1

```
ccgagaccat gggcaactac cacccgcacg gcgacgcgtc gatctacgac agcctggtgc      60
gcatggccca gccctggtcg ctgcgctacc cgctggtgga cggccaggg              109
```

<210> SEQ ID NO 2
<211> LENGTH: 109
<212> TYPE: DNA
<213> ORGANISM: Mycobacterium tuberculosis

<400> SEQUENCE: 2

-continued

```
ccgagaccat gggcaactac cacccgcacg gcgacgtgtc gatctacgac accctggtgc      60
gcatggccca gccctggtcg ctgcgctacc cgctggtgga cggccaggg                 109
```

<210> SEQ ID NO 3
<211> LENGTH: 109
<212> TYPE: DNA
<213> ORGANISM: Mycobacterium tuberculosis

<400> SEQUENCE: 3

```
ccgggaccat gggcaactac cacccgcacg gcgacgcgtc gatctacgac agcctggtgc      60
gcatggccca gccctggtcg ctgcgctacc cgctggtgga cggccaggg                 109
```

<210> SEQ ID NO 4
<211> LENGTH: 109
<212> TYPE: DNA
<213> ORGANISM: Mycobacterium tuberculosis

<400> SEQUENCE: 4

```
ccgagaccat gggcaactac cacccgcacg gcgacgcgtc gatctacgac agcctggtgc      60
gcatggccca gccctggtcg ctgcgctacc cgctggcgga cggccaggg                 109
```

<210> SEQ ID NO 5
<211> LENGTH: 109
<212> TYPE: DNA
<213> ORGANISM: Mycobacterium tuberculosis

<400> SEQUENCE: 5

```
ccgagaccat gggcaactac ccccgcacg gcgacgcgtc gatctacgac agcctggtgc       60
gcatggccca gccctggtcg ctgcgctacc cgctggtgga cggccaggg                 109
```

<210> SEQ ID NO 6
<211> LENGTH: 109
<212> TYPE: DNA
<213> ORGANISM: Mycobacterium tuberculosis

<400> SEQUENCE: 6

```
ccgagaccat gggcaactcc cacccgcccg gcgacgcgtc gatctacgac agcctggtgc      60
gcatggccca gccctggtcg ctgcgctacc cgctggtgga cggccaggg                 109
```